(12) United States Patent
Popescu et al.

(10) Patent No.: US 8,548,554 B2
(45) Date of Patent: Oct. 1, 2013

(54) DRY ELECTRODE CAP FOR ELECTRO-ENCEPHALOGRAPHY

(75) Inventors: Florin Popescu, Berlin (DE); Siamac Fazli, Berlin (DE); Yakob Badower, London (GB); Klaus R. Mueller, Berlin (DE)

(73) Assignee: Fraunhofer-Gesellschaft zur Forderung der angewandten Forschung e.V., Munich (DE)

( * ) Notice: Subject to any disclaimer, the term of this patent is extended or adjusted under 35 U.S.C. 154(b) by 684 days.

(21) Appl. No.: 12/517,664

(22) PCT Filed: Dec. 8, 2006

(86) PCT No.: PCT/EP2006/011843
§ 371 (c)(1),
(2), (4) Date: Mar. 23, 2010

(87) PCT Pub. No.: WO2008/067839
PCT Pub. Date: Jun. 12, 2008

(65) Prior Publication Data
US 2010/0198042 A1    Aug. 5, 2010

(51) Int. Cl.
*A61B 5/0478* (2006.01)
(52) U.S. Cl.
USPC .............................. 600/383; 600/393; 600/544
(58) Field of Classification Search
USPC .......................................... 600/383, 544, 393
See application file for complete search history.

(56) References Cited

U.S. PATENT DOCUMENTS

| | | | | |
|---|---|---|---|---|
| 2,426,958 A | * | 9/1947 | Ulett, Jr. et al. | 600/383 |
| 3,735,753 A | * | 5/1973 | Pisarski | 600/383 |
| 3,896,790 A | * | 7/1975 | Dikmen | 600/383 |
| 4,084,583 A | | 4/1978 | Hjort | |
| 4,350,164 A | | 9/1982 | Allain | |
| 4,709,702 A | * | 12/1987 | Sherwin | 600/383 |
| 4,928,696 A | | 5/1990 | Henderson et al. | |
| 5,331,969 A | | 7/1994 | Silberstein | |
| 6,961,603 B2 | * | 11/2005 | Merilainen | 600/383 |
| 2002/0177767 A1 | | 11/2002 | Burton et al. | |
| 2002/0182574 A1 | | 12/2002 | Freer | |

FOREIGN PATENT DOCUMENTS

| | | |
|---|---|---|
| EP | 0232102 | 1/1987 |
| EP | 0541393 | 11/1992 |
| EP | 0 541 393 A1 | 5/1993 |
| EP | 1488740 | 12/2004 |
| GB | 818711 | 1/1957 |
| GB | 1322472 | 1/1972 |
| WO | WO2005/086574 | 9/2005 |

OTHER PUBLICATIONS

International Search Report and Written Opinion for PCT/EP2006/011843 completed Nov. 28, 2007.
Griss, P., et al., "Characterization Of Micromachined Spiked Biopotential Electrodes", Jun. 2002, Biomedical Engineering, IEEE Transactions, vol. 49, Issue: 6, pp. 597-604.
Official action in related JP 2009-539609 dated Nov. 15, 2011, 5 pages.

* cited by examiner

*Primary Examiner* — Lee S Cohen
(74) *Attorney, Agent, or Firm* — Barnes & Thornburg LLP (57) ABSTRACT

An electro-encephalography electrode cap for contacting the scalp of a head with a number of pin-shaped electrodes for contacting the scalp, and an electrode holding device. The electrodes are mounted on the electrode-holding device through at least one elastic joint.

6 Claims, 9 Drawing Sheets

DRY ELECTRODE CAP FOR ELECTRO-ENCEPHALOGRAPHY

CROSS REFERENCE TO RELATED APPLICATIONS

This application is the U. S. national phase of PCT/EP2006/011843 filed Dec. 8, 2006. The disclosure of PCT/EP2006/011843 is hereby incorporated herein by reference.

The invention relates to an electrode cap for electro-encephalography which allows contacting the head of a human or an animal without a conductive gel between the scalp and the electrode itself.

The most common non-invasive solution to collect electro-encephalography (EEG) data, applied in biomedical research and hospitals, is the wet electrode, comprising a metal plate coated with Ag. This wet electrode requires gel to be applied between the skin and the electrode to allow for the exchange of ions at the interface. The use of such a gel is inconvenient for a daily use of the electrodes: it requires a time consuming preparation before any EEG recording can be carried out; the gel dries with the passing of time and thus needs to be refilled in long applications of the electrodes to the scalp. It has also been reported that long term contact with the skin produces irritation.

An alternative approach to the collection of EEG data is the use of sensors that operate with current displacement, that is a capacitive transduction, instead of charge current, as was the case for the previous example. These types of electrodes do not require physical contact to the signal source. However, the advantage of independence of contact with the body brings along the disadvantage that the background noise recorded along with the physiological signals is higher.

All other solutions make contact with the skin. Some make use of NASICON ceramic material. The particular propriety of interest of the NASICON (acronym for Na Super Ionic Conductor) material is its very high conductivity of $Na^+$ ions even at room temperature. The downside of using this material is a higher impedance mismatch with the skin than the common wet electrodes.

Microfabrication technology has produced good results in miniaturization of real size sensors. As interesting examples, Griss et al. developed a dry electrode that avoids the use of electrolytic gel and at the same time fixes the electrode to the skull surface with enough reliability to avoid motion artifacts, making use of microfabricated spikes on the electrode surface (Griss, P et al., "Characterization of micromachined spiked biopotential electrodes", Biomedical Engineering, IEEE Transactions on Volume 49, Issue: 6 Jun. 2002).

There is a higher potential difference measured between a pair of such electrodes than in the case of the standard wet electrodes which could be due to the influence of the potential of the sweating duct membranes in the dermis. Despite this fact, it seems that sweat on the skin does not produce so much variation on the electrode impedance as occurs with Ag/AgCl electrodes. The spikes prickle the outer layers of the skin but avoid penetrating the dermis, where nerves and blood vessels are. This way, pain-free measurements of potentials is achieved, avoiding the high impedance from the outer skin layers.

Another solution makes use of carbon nanotubes. In a similar configuration, a population of carbon nano-tubes are used as probes that, in pricking the surface layers of the dermis, behave as the transducers themselves.

It is therefore the problem to be solved by the present invention to provide an easily manufacturable, affordable device which can be placed on the head in a few minutes, is comfortable, makes reliable long-term skin contact without pain, and provides enough accuracy in recording of brain activity for applications such as for example brain-computer interfaces.

The present invention is based on the idea that an optimal result of an electro-encephalography measurement (EEG) together with a maximum of wearing comfort for the patient is achieved if the force that each pin exerts on the scalp of the patient is uniform for all electrodes or groups of electrodes and can be adjusted.

According to the present invention, this is achieved by mounting or supporting the electrodes on an electrode holding means through at least one elastic joint. The electrodes push down onto the surface of the scalp by means of an elastic force, as for example that of a spring or of pneumatic pressure.

The electrode holding means preferably comprises a head-fixing means, such as for example an adjustable head strap which tightens around the forehead, side and back of the head and allows to fix the electrode cap to the head with adjustable pressure.

Preferably, the electrodes are mounted on the electrode holding means through one or more connecting means which preferably are or comprise a small number, for example 2 to 30, holding arms. As many arms can be used as can be fit without interfering with each other physically. Those holding arms are fixed to the head fixing means or head strap with one end while the other end carries the electrodes. The electrodes can be attached to the holding arms directly or indirectly through other components.

It is preferred that the holding arms comprise two legs which are connected with each other through an elastic joint. The lower part of the arm, that is the leg which is connected to the head fixing means, is called electrode arm support. To this an electrode arm moving beam, that is the leg which carries the electrodes, is attached by means of a revolute or prismatic joint. Preferably, this allows the distal end of the arm to move perpendicularly to the surface of the scalp. If the legs of the arms are straight they preferably include an angle which opens in the direction of the head. The elastic joint between the legs of an arm can be a revolute joint or a pivotal joint of which the rotation axis is perpendicular to the length of the legs and tangential to the head.

It is preferred that a torque-producing flexing cord or a similarly adjustable torsional spring is stretched between pairs of adjacent legs of an arm which are connected with each other by an elastic joint. This allows to apply a bending moment around this elastic joint which connects the two legs. By adjusting the length of such a cord or spring, the pressure which the electrodes apply to the scalp of the head can be adjusted. The cord or spring may have a certain elastic stiffness $K_{EAFC}$ and zero point $X_{0EAFC}$ either of which may be adjustable by hand via a tightening screw or a geared mechanism.

It is also possible that the joint between two adjacent legs is a prismatic joint which is preferably movable in the direction of the head of the patient. Such a prismatic joint comprises a bore or cylinder in one leg in which a part of the other leg is guided in one direction, for example the direction of the length of the leg.

Between the two legs, a spring or some other flexible element can be arranged, which expands or contracts if the legs are moved against each other. It is furthermore possible to connect two neighbouring legs of an arm by a flexing cord, similarly as outlined for the pivotal joint, above. By this a force is applicable in the direction in which the prismatic joint is movable. This force can act in the direction of the elastic force of the elastic element or in the opposite direction. By adjusting the length of such a cord, the pressure which the electrodes apply to the scalp of the head can be adjusted. This cord also may have a certain elastic stiffness $K_{EAFC}$ and zero point $X_{0EAFC}$ either of which may be adjustable by hand via a tightening screw or a geared mechanism.

Preferably, the individual electrodes are grouped into groups whereby each group comprises a part of the electrodes. The number of electrodes in each group is preferably equal but can also be different.

Electrodes which belong to the same group are held by a common group holding means which holds all electrodes of this group. The group holding means are each mounted directly or indirectly on the electrode holding means through at least one elastic joint. As explained above this holding means can be an electrode holding arm wherein the different legs are connected through elastic joints.

The group holding means preferably comprise at least one elastic joint through which they are mounted on the electrode holding means or the holding arm. Such an elastic joint can be a semi-rigid spherical joint or a virtual ball joint which is an elastic structure which, through its elasticity, provides the same motion as a ball joint on the distal end of a leg attached to the joint. Its response to deflections is equivalent to that of a spring-loaded ball joint. Such a joint can be movable around a first axis parallel to the length of the electrodes, i.e. parallel to the direction of the force by which the electrodes are pressed against the head. For this direction, the joint then has a certain torsional stiffness $K_S$. It is furthermore possible that the joint is movable around at least one axis perpendicular to the direction in which the force acts which applies pressure to the head. In this direction, the joint has a torsional stiffness $K_T$. If the joint is movable around an axis perpendicular to the length of the electrodes, the surface which is described by the tips of the electrodes can adjust its orientation to the slope of the head at the position where the electrodes are applied. It is preferred that the torsional stiffness around the axis perpendicular to the length of the electrodes $K_T$ is considerably greater than the torsional stiffness $K_S$ around the axis parallel to the length of the electrodes. By this, the group holding means can be prevented from rotating excessively around a direction normal to the scalp surface.

Preferably, the electrodes of a given group are grouped into sub-groups or bundles which each contain the same number of electrodes or a similar number of electrodes with parallel lengths. The electrodes are perpendicular to the surface on which they are located. There may exist two, three or more bundles of electrodes in one group. Within a bundle, the electrodes can be arranged in a shape which has a circular, elliptical, triangular or rectangular outline. The electrodes within a bundle can be arranged in concentrical circuits or some electrodes can be arranged around a center electrode. However, also other arrangements of the electrodes within a bundle are possible. If necessary, the electrodes can be arranged in bundle holding means which may be arranged at the group holding means through a joint which may be an elastic joint. If the electrodes are bundled the contact to the skin is ensured despite hair and surface irregularities. Each additional pin adds more potential contact surface between metal and skin, thus lowering the effective electrode impedance.

A group holding means can comprise two, three or more bundles of electrodes. If there are three bundles, those can be located at the corners of a triangle, preferably an equilateral triangle. In this configuration, the group holding means can have a Y-structure, i.e. a structure with three straight legs which meet with one end at one point and preferably have the same length. The angles between the legs are preferably all equal.

An Y-shaped group holding means allows each branch of the Y to make contact with the scalp independently, as the spherical joint allows.

The relative stiffness among electrodes in a bundle is high, while the stiffness of the moving beam of the entire bundle's electrode arm is relatively low.

If the bundles have three electrodes, those can also be placed at the corners of a triangle, which is preferably an equilateral triangle. The centre of this triangle marks the location of the bundle.

It is preferred that each single electrode is elastically supported. Hereby, the electrodes can be guided in a guide member which guides the electrodes in the axial direction of their length, that is basically in the direction of the scalp. Within the guides the electrodes are supported on an elastic element which is elastic in the direction in which the electrodes can move in the guide. The electrode is thus arranged like a piston in a cylinder. The elastic element can be a spring which is placed inside the guide member behind the electrode in direction of the axial length of the electrode.

Alternatively, the electrodes can be virtually compressible, i.e. they are elastically deformable. Here the electrodes can be thin metal pins.

It is preferred that the electrodes are coated or plated in a high conductance material, such as for example gold, platinum, silver, silver chloride other precious metals, alloys and/or conductive nanoparticles.

The electrodes are intended to measure electrical signals in an electro-encephalography. For this purpose, the electrodes can be wired in unipolar configuration in which all pins in a bundle are in contact with each other. A voltage can then be measured with reference to ground. Alternatively, the electrodes can be arranged in a bipolar configuration where the electrodes of a bundle, a group or all electrodes are separated into two groups, wherein the electrodes of one group are electrically connected with each other and the electrodes of the other group are connected electrically with each other so that a voltage between the electrodes of the two groups can be measured.

DETAILED DESCRIPTION OF THE DRAWINGS

Figure 1:
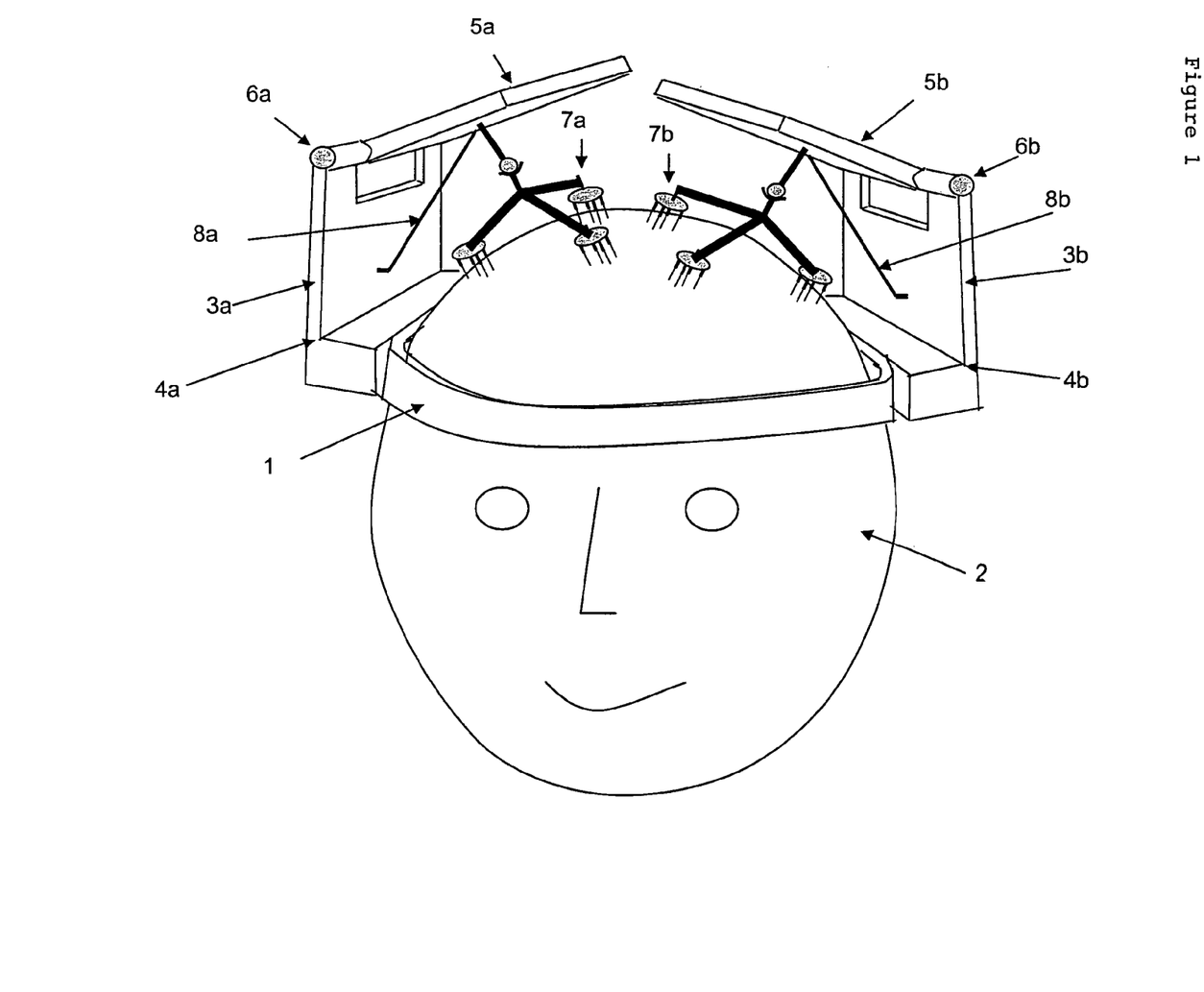
FIG. 1 shows an electrode cap according to the present invention mounted on the head of a patient.

FIG. 1 shows an electrode cap according to the present invention mounted on the head 2 of a person. The electrode cap comprises a head strap 1 which runs around the head 2. On opposite sides of the head strap 1, two holding arms 3a and 3b are attached. The holding arms 3a and 3b each comprise two legs 4a and 5a as well as 4b and 5b which are connected with each other through revolute joints 6a, 6b. The lower legs 4a and 4b, which are supporting legs, are attached to the head strap 1 with one side and to the joints 6a and 6b, respectively, with the other side. The second legs 5a and 5b, which are electrode arm moving beams, carry group holding means 7a, 7b. Those have the form of 3-branch-trees on which three bundles of electrodes are accommodated at the ends of its legs.

The electrode arm support 4a, 4b and the electrode arm moving beam 5a, 5b are each arranged at an angle which opens in the direction of the head. Between the two legs 4a and 5a as well as 4b and 5b, a flexing cord 8a, 8b is stretched. By these flexing cords 8a, 8b, the pressure by which the electrodes are pushed on the head 2 is adjustable.

Figure 2:
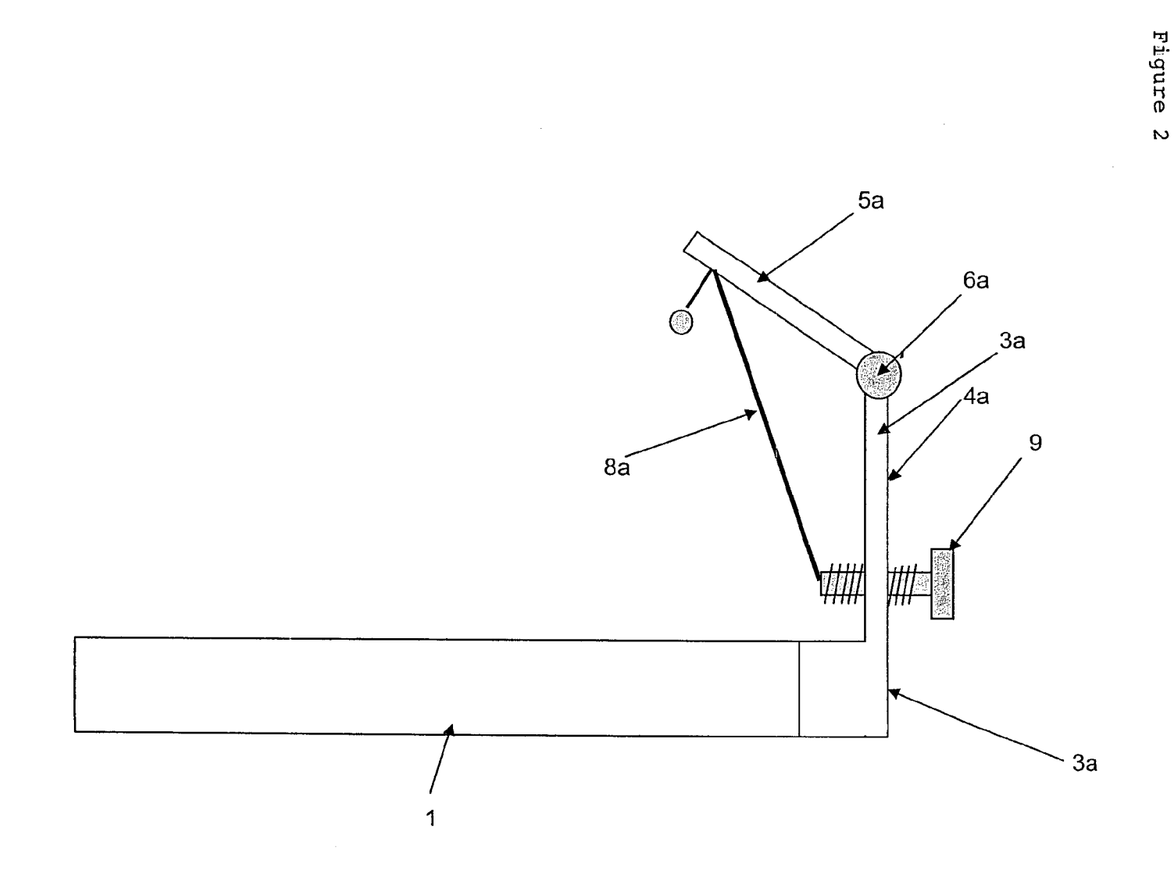
FIG. 2 shows a head strap with a holding arm which comprises a pivotal joint.

FIG. 2 shows the electrode arm 3a in detail. The electrode arm 3a is mounted on the head strap 1. It comprises a first leg 4a and a second leg 5a which are connected with each other through a pivotal joint 6a. Between the electrode arm support 4a and the electrode arm moving beam 5a, a flexing cord 8a is stretched which bends the electrode arm 3a around the joint 6a. The angle between the legs 4a and 5a is adjustable by changing the tension of the string 8a. The flexing cord 8a may be elastic itself with an elastic stiffness $K_{EAFC}$. The tension of the cord 8a can be adjusted by hand with the tightening screw 9.

Figure 3:
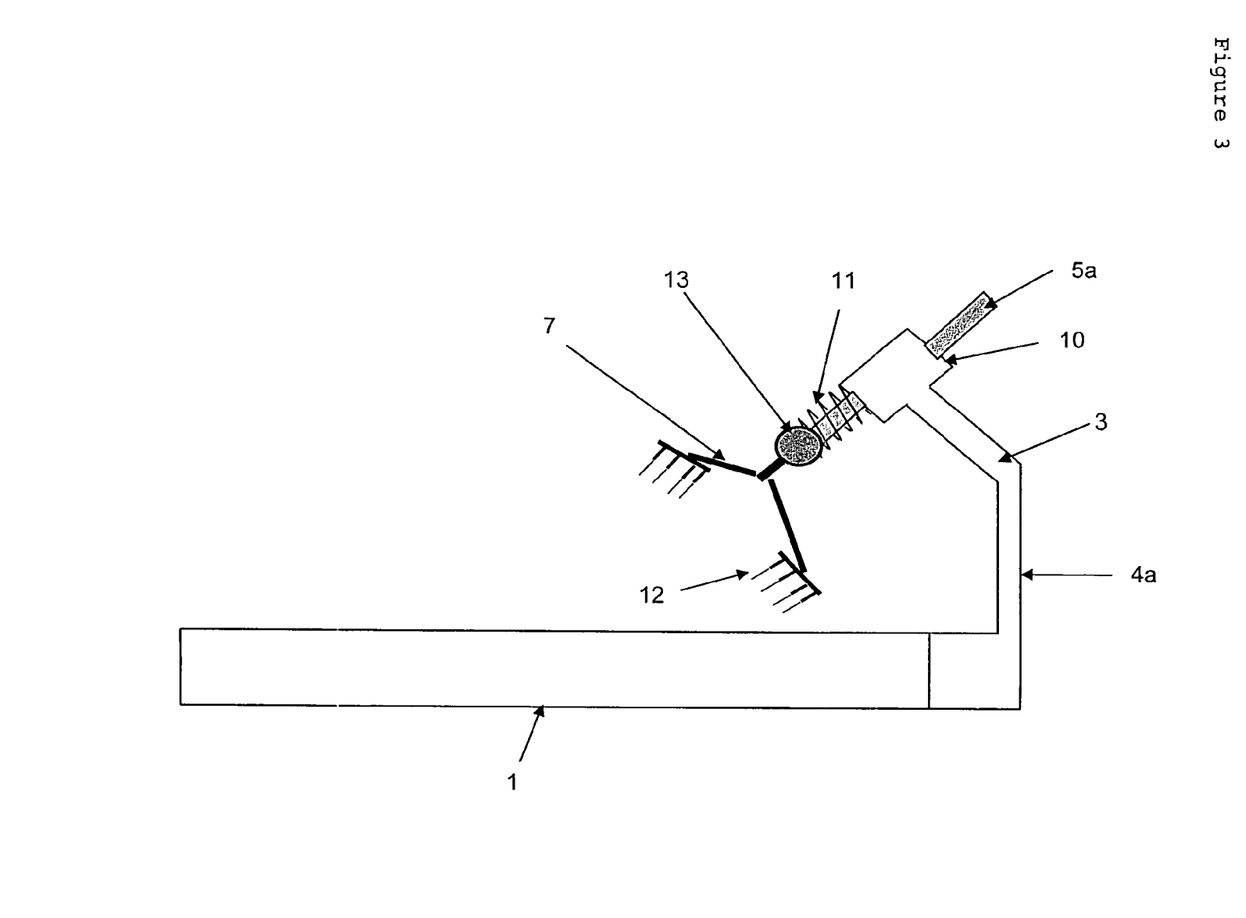
FIG. 3 shows a head strap with a holding arm which comprises a prismatic joint.

FIG. 3 shows an alternative construction of the arm 3 which corresponds to the arms 3a and 3b in the previous figures. The first leg 4a, which is the electrode arm support, is connected with the second leg 5a via a prismatic joint 10. The prismatic joint 10 is given by a drilling in the first arm 4a in which the second arm 5a is guided in the direction of its length.

Again, the legs 4a and 5a build an angle which opens in the direction of the head. Also the electrode arm support may have an angle, opening in the direction of the head. The second arm 5a carries a group holding means 7 through a semi-rigid spherical joint 13. The group holding means 7 carries the electrodes 12. Between the group holding means 7 and the first arm 4a, a spring 11 is located parallely to the second arm 5a, preferably surrounding the second arm 5a. This spring 11 therefore contracts or expands if a force is applied on the second arm 5a in the direction of its length. This happens for example when the electrodes 12 are pressed against the head of a patient.

Figure 4:
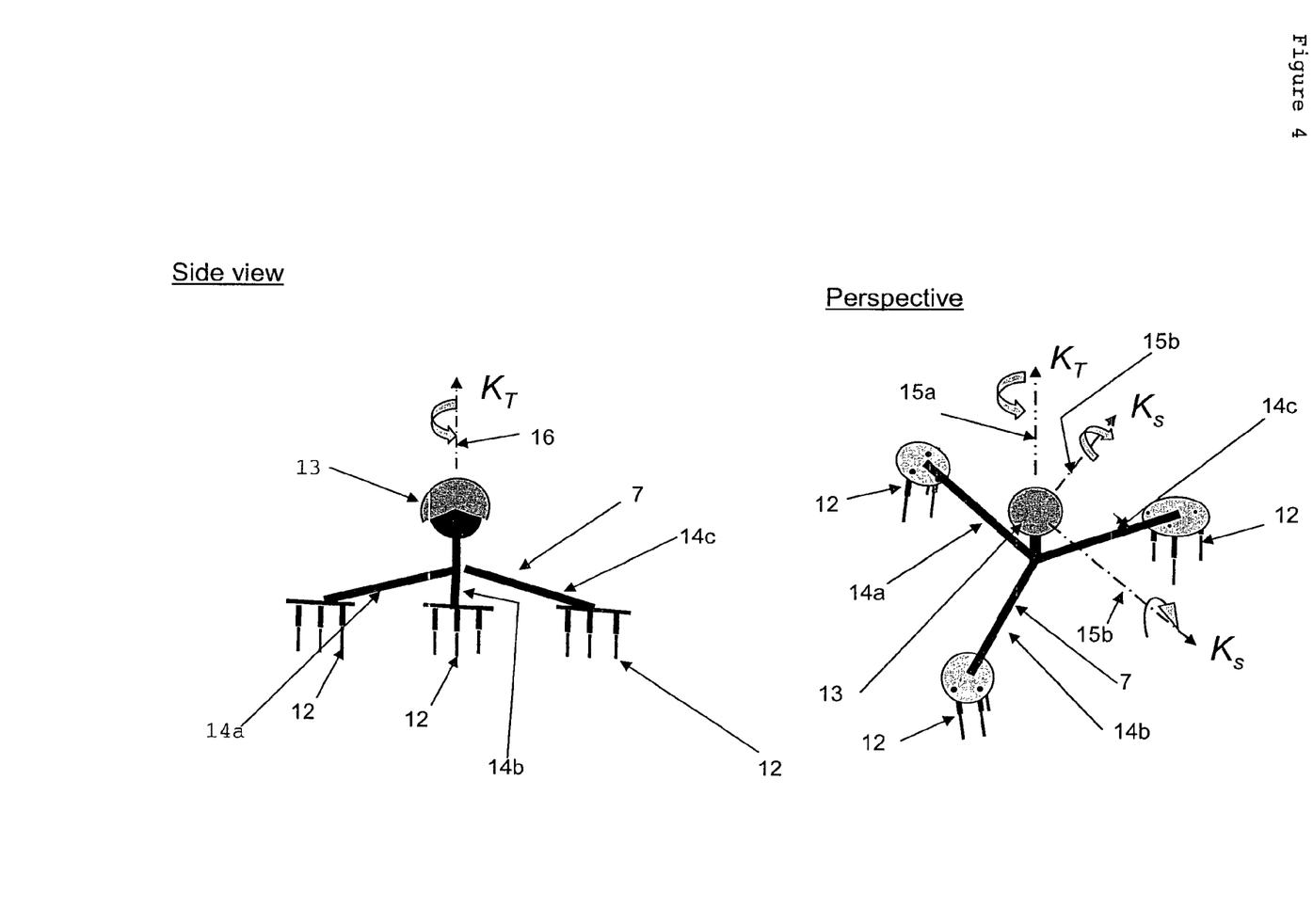
FIG. 4 shows a group holding means with three bundles of electrodes.

FIG. 4 shows a group holding means carrying three bundles of electrodes 12. Each bundle comprises three electrodes 12 which are located at the corners of an triangle, for example an equilateral triangle. The upper part of the figure shows the view perpendicular to the length of the electrodes while the lower part of the figure shows a view from above. It can be seen from the lower part of the figure, that the group holding means 7 has a Y-structure with three legs 14a, 14b, 14c of equal length which are arranged in equal angles to each other. The holding structure 7 has a semi-rigid spherical joint 13 through which it is connected with the holding arm 3.

The semi-rigid spherical joint 13 is elastically movable around an axis 16 which is parallel to the electrodes 12 as well as one or two axises 15a and 15b which are perpendicular to the direction of the electrodes 12. The torsional stiffness $K_T$ of the first axis is considerably greater than that of the second axis $K_S$, in a similar manner as torques produced in response to motion by an elastic U-joint.

Figure 5:
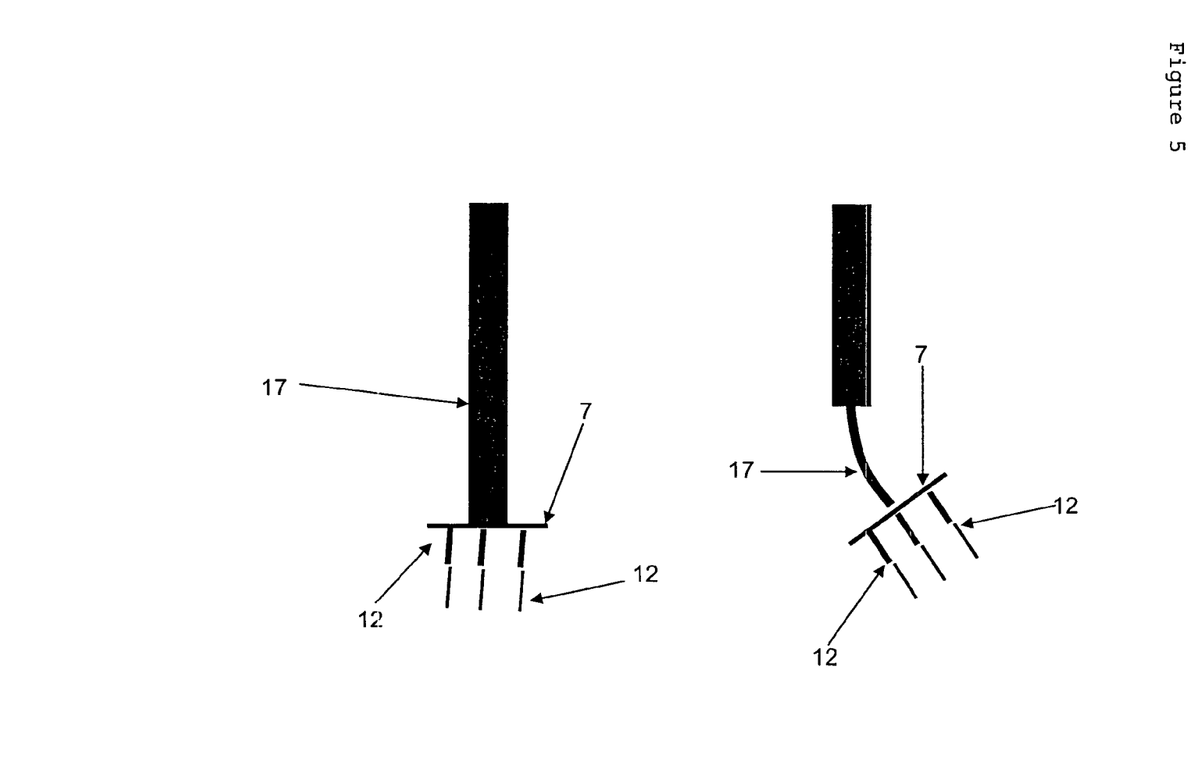
FIG. 5 shows a group holding means which is deformable around an axis parallel to the length of the electrodes.

FIG. 5 shows an alternative construction of the group holding means 7. Here, the holding means 7 is fixed at a virtual ball joint 17. A virtual ball joint is an elastic structure which, through its elasticity, provides the same motion as a ball joint on the distal end of an leg attached to the joint. Its response to deflections is equivalent to that of a spring-loaded ball joint.

The element 17 is bendable around at least one axis perpendicular to the electrodes 12 and may also be flexible around an axis parallel to the electrodes 12.

Figure 6:
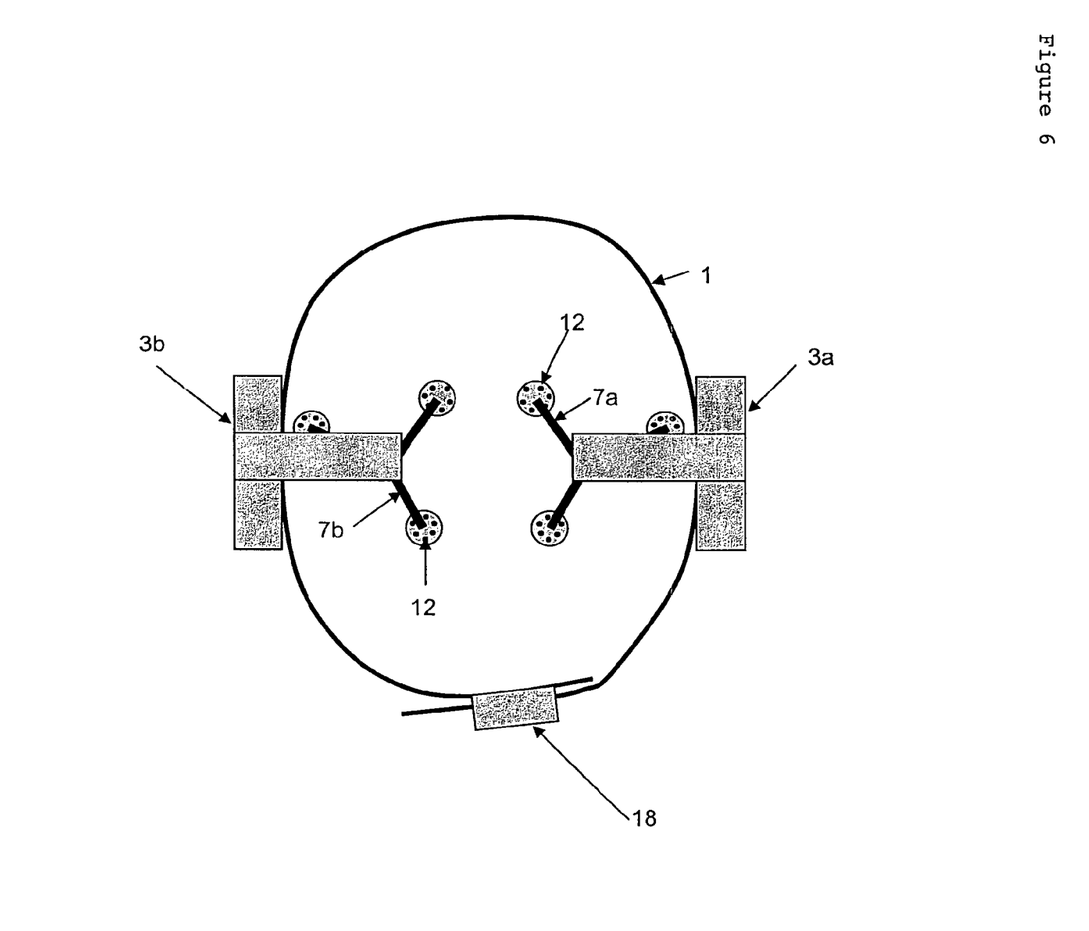
FIG. 6 shows an electrode cap mounted on the head of a patient viewed from above.

FIG. 6 shows an electrode cap according to the present invention viewed from above the head of the patient. The shown configuration is a sample for BCI applications that utilize motor imagery. The head strap 1 runs around the head of the patient and is closed with a closing means 18. This may allow the adjustment of the head strap 1. The electrode arms 3a and 3b carry the group holding means 7a and 7b at which the electrodes 12 are arranged. In the shown example, the group holding means 7a and 7b have the Y-structure as described above. The configuration allows access to the central and lateral regions of the scalp and therefore the brain.

Figure 7:
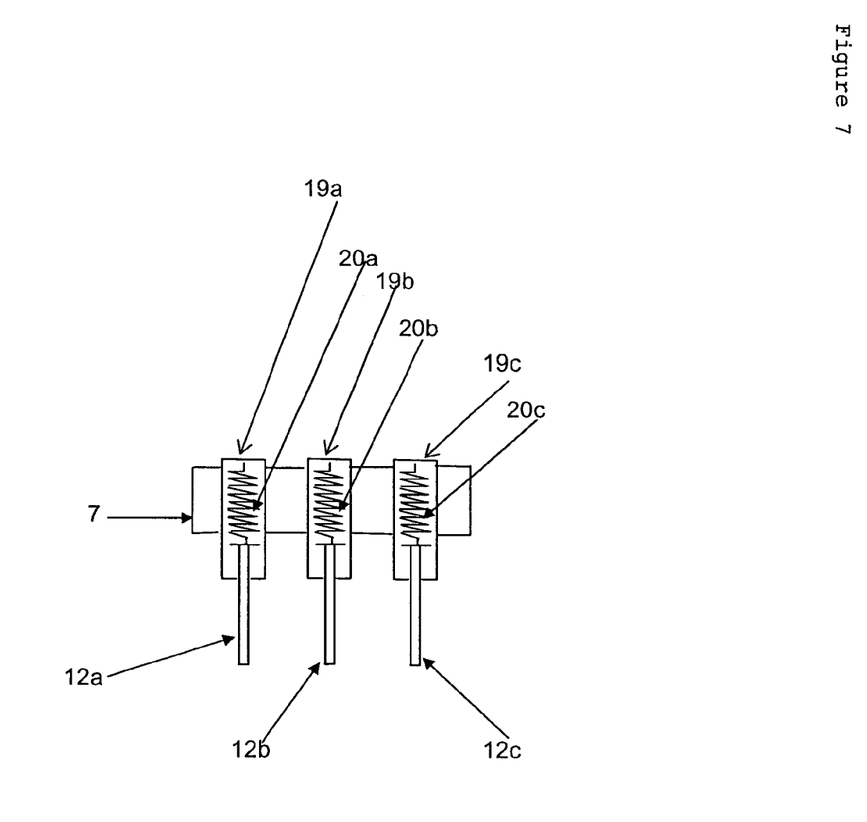
FIG. 7 shows three elastically supported electrodes.

FIG. 7 shows electrodes which are elastically supported along their axis by means of moving parts and elastic elements. The electrodes 12a, 12b and 12c are located in a holding means 7 and are each located in guide members 19a, 19b and 19c which only allow the electrodes to move in the direction of their axial length. The electrodes are supported in contact with elastic elements, as for example springs 20a, 20b and 20c, which are fixed at the guiding means 19a, 19b, 19c with one end and are in contact with the electrodes 12a, 12b and 12c with the other end, respectively. The electrodes 12a, 12b and 12c can therefore move in the cylindrical tubes 19a, 19b and 19c like a piston in a cylinder. The example only shows three electrodes, however, any number of electrodes can be placed in a bundle, a group or the electrode cap.

Figure 8:
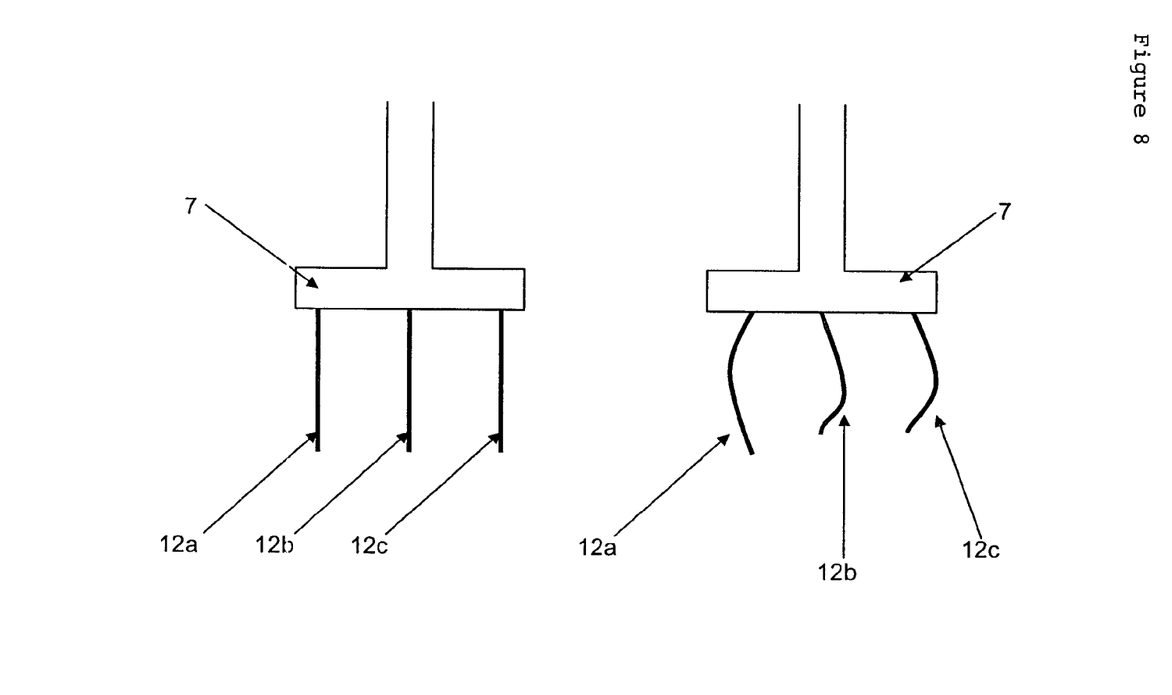
FIG. 8 shows virtually compressible electrodes mounted on a group holding means.

FIG. 8 shows virtually compressible electrodes as an alternative for elastically supported electrodes. The left part of FIG. 8 shows those electrodes 12a, 12b, 12c mounted on a holding means 7 if no force is applied to the electrodes. The right side of FIG. 8 shows the same setup if force is applied to the electrodes 12a to 12c. Here, the electrodes are elastical themselves, i.e. they bend elastically when a force is applied. In other words, the electrodes can deflect in similar means as above by the flexibility of the shape and material from which they are made.

Figure 9:
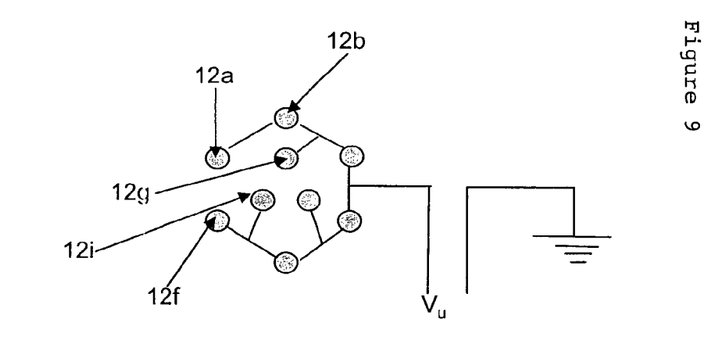
FIG. 9 shows a unipolar configuration of an electrode bundle.

FIG. 9 shows a unipolar configuration of electrodes in a bundle. Six electrodes 12a to 12f are grouped around three electrodes 12g to 12i. All electrodes are electrically connected with each other and a voltage $V_u$ is measurable with reference to ground.

Figure 10:
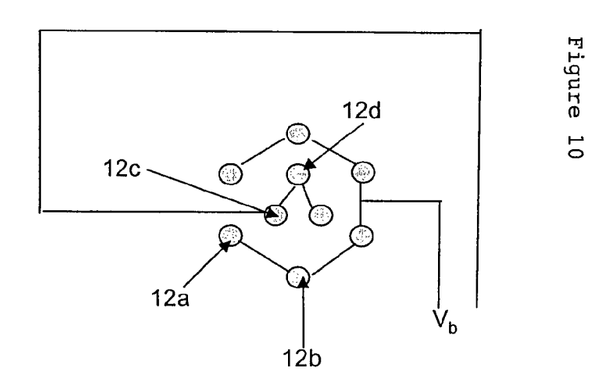
FIG. 10 shows a bipolar configuration of the electrodes in a bundle.

FIG. 10 shows a bipolar configuration of electrodes in a bundle. The electrodes are grouped into two parts, which form the two poles between which the voltage $V_b$ is measurable. The electrodes 12a and 12b belong to one pole while the electrodes 12c and 12d belong to the other pole. The electrodes of each part are electrically connected with each other.

The electrode cap according to the present invention is applicable wherever electro-encephalography recordings are desirable with minimal preparation and long duration, that is duration longer than, e.g. two hours. Those are for example medical diagnosis and monitoring, brain-computer-interfaces (BCI), lie detection or monitoring of user attention in safety-critical operation of machines. The electrode cap according to the present invention does not require conductive gel between the scalp and the electrodes and the force that each electrode pin exerts on the scalp is uniform and does not cause pain to the patient while the electrodes are in stable contact with the skin. The overall level of force or the force applied by certain groups of electrodes is adjustable.

The invention claimed is:

1. An electrode cap for contacting the scalp of a head in an electro-encephalography with a number of pin-shaped electrodes for contacting the scalp, and an electrode holding means wherein the electrodes are mounted on the electrode-holding means through at least one first elastic joint, the electrodes being grouped into at least one group, the electrodes of each group being mounted on a common group-holding means and the group-holding means each being mounted on the electrode-holding means through at least one second elastic joint through which the electrodes comprising the group are mounted on the electrode-holding means.

2. The electrode cap according to claim 1 wherein the second elastic joint is at least one of a semi-rigid spherical joint and a virtual ball joint which is at least one of movable around a first axis parallel to the length of the electrodes of this group with a torsional stiffness $K_s$ and movable around at least one axis perpendicular to the length of the electrodes with a torsional stiffness of $K_T$.

3. The electrode cap according to claim 2 wherein $K_T$ is greater than $K_S$.

4. An electrode cap for contacting the scalp of a head in an electro-encephalography with a number of pin-shaped electrodes for contacting the scalp, and an electrode holding means wherein the electrodes are mounted on the electrode-holding means through at least one first elastic joint, the electrodes being grouped into at least one group, the electrodes of each group being mounted on a common group-holding means and the group-holding means each being mounted on the electrode-holding means through at least one second elastic joint, the electrodes of at least one group being grouped into three bundles which are located at the corners of a triangle.

5. The electrode cap according to claim 4 wherein the group-holding means has a Y-structure, whereby the three bundles are located at the ends of the legs of the Y-structure.

6. An electrode cap for contacting the scalp of a head in an electro-encephalography with a number of pin-shaped electrodes for contacting the scalp, and an electrode holding means wherein the electrodes are mounted on the electrode-holding means through at least one first elastic joint, the electrodes being grouped into at least one group, the electrodes of each group being mounted on a common group-holding means and the group-holding means each being mounted on the electrode-holding means through at least one second elastic joint, the electrodes of at least one group being grouped into at least two bundles, each bundle having three electrodes which are located at the corners of a triangle.

* * * * *

UNITED STATES PATENT AND TRADEMARK OFFICE
CERTIFICATE OF CORRECTION

PATENT NO. : 8,548,554 B2  Page 1 of 1
APPLICATION NO. : 12/517664
DATED : October 1, 2013
INVENTOR(S) : Popescu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 972 days.

Signed and Sealed this
Fifteenth Day of September, 2015

Michelle K. Lee
*Director of the United States Patent and Trademark Office*